United States Patent [19]

Lesage et al.

[11] Patent Number: 6,013,470
[45] Date of Patent: Jan. 11, 2000

[54] FAMILY OF MAMMALIAN POTASSIUM CHANNELS, THEIR CLONING AND THEIR USE ESPECIALLY FOR THE SCREENING OF DRUGS

[75] Inventors: Florian Lesage; Eric Guillemare, both of Nice; Michel Fink, Cannes La Bocca; Fabrice Duprat, Valluris; Michel Lazdunski, Nice; Georges Romey, Nice; Jacques Barhanin, Nice, all of France

[73] Assignee: Centre National de la Recherche Scientifique-CNRS, Paris, France

[21] Appl. No.: 08/749,816

[22] Filed: Nov. 15, 1996

[30] Foreign Application Priority Data

Feb. 8, 1996 [FR] France .................................. 96 01565

[51] Int. Cl.[7] ........................... C12P 21/06; C12N 15/00; C12N 15/63; C07H 21/02
[52] U.S. Cl. ..................... 435/69.1; 435/320.1; 435/325; 536/23.1
[58] Field of Search ................................ 435/69.1, 320.1; 514/44; 536/23.5

[56] References Cited

FOREIGN PATENT DOCUMENTS

WO 94/28131  12/1994  WIPO .

OTHER PUBLICATIONS

Ketchum et al. Nature. 376, 690–694, Aug. 1995.
Lesage et al. Genomics 34, 153–155, 1996.

Primary Examiner—Paula K. Hutzell
Assistant Examiner—Lin Sun-Hoffman
Attorney, Agent, or Firm—Weiser and Associates, P.C.

[57] ABSTRACT

The present invention relates to the cloning of a member of a new potassium channel named TWIK-1. More specifically, it relates to an isolated and purified nucleic acid molecule coding for a protein constituting a potassium channel exhibiting the properties and structure of the TWIK-1 type channel, as well as the protein coded by this nucleic acid molecule.

The invention also relates to the use of this nucleic acid molecule to transform cells, and the use of these cells expressing the potassium channels exhibiting the properties and structure of the TWIK-1 type channel for the screening of drugs.

15 Claims, 11 Drawing Sheets

```
                                              gggcaggaagacggcgctgcccggaggagc  -153
ggggcgggcgggcgcgcggggggagcgggcggcgggcgggagccaggcccgggcgggggcggggcggcggggccag  -77
aagaggcggcgggccgcgctccggccggtctgcggcgttggccttggctttggcggcggcggtggagaag        -1
```

| ATG | CTG | CAG | TCC | CTG | GCC | GGC | AGC | TCG | TGC | GTG | CGC | CTG | GTG | GAG | CGG | CAC | CGC | TCG | 57 |
|---|---|---|---|---|---|---|---|---|---|---|---|---|---|---|---|---|---|---|---|
| M | L | Q | S | L | A | G | S | S | C | V | R | L | V | E | R | H | R | S | 19 |

| GCC | TGG | TGC | TTC | GGC | TTC | CTG | GTG | CTG | GGC | TAC | TTG | CTC | TAC | CTG | GTC | TTC | GGC | GCA | 114 |
|---|---|---|---|---|---|---|---|---|---|---|---|---|---|---|---|---|---|---|---|
| A | W | C | F | G | F | L | V | L | G | Y | L | L | Y | L | V | F | G | A | 38 |

| GTG | GTC | TTC | TCC | TCG | GTG | GAG | CTG | CCC | TAT | GAG | GAC | CTG | CTG | CGC | CAG | GAG | CTG | CGC | 171 |
|---|---|---|---|---|---|---|---|---|---|---|---|---|---|---|---|---|---|---|---|
| V | V | F | S | S | V | E | L | P | Y | E | D | L | L | R | Q | E | L | R | 57 |

| AAG | CTG | AAG | CGA | CGC | TTC | TTG | GAG | GAG | CAC | GAG | TGC | CTG | TCT | GAG | CAG | CAG | CTG | GAG | 228 |
|---|---|---|---|---|---|---|---|---|---|---|---|---|---|---|---|---|---|---|---|
| K | L | K | R | R | F | L | E | E | H | E | C | L | S | E | Q | Q | L | E | 76 |

| CAG | TTC | CTG | GGC | CGG | GTG | CTG | GAG | GCC | AGC | AAC | TAC | GGC | GTG | TCG | GTG | CTC | AGC | AAC | 285 |
|---|---|---|---|---|---|---|---|---|---|---|---|---|---|---|---|---|---|---|---|
| Q | F | L | G | R | V | L | E | A | S | N | Y | G | V | S | V | L | S | N | 95 |

| GCC | TCG | GGC | AAC | TGG | AAC | TGG | GAC | TTC | ACC | TCC | GCG | CTC | TTC | TTC | GCC | AGC | ACC | GTG | 342 |
|---|---|---|---|---|---|---|---|---|---|---|---|---|---|---|---|---|---|---|---|
| A | S | G | N | W | N | W | D | F | T | S | A | L | F | F | A | S | T | V | 114 |

| CTC | TCC | ACC | ACA | GGT | TAT | GGC | CAC | ACC | GTG | CCC | TTG | TCA | GAT | GGA | GGT | AAG | GCC | TTC | 399 |
|---|---|---|---|---|---|---|---|---|---|---|---|---|---|---|---|---|---|---|---|
| L | S | T | T | G | Y | G | H | T | V | P | L | S | D | G | G | K | A | F | 133 |

| TGC | ATC | ATC | TAC | TCC | GTC | ATT | GGC | ATT | CCC | TTC | ACC | CTC | CTG | TTC | CTG | ACG | GCT | GTG | 456 |
|---|---|---|---|---|---|---|---|---|---|---|---|---|---|---|---|---|---|---|---|
| C | I | I | Y | S | V | I | G | I | P | F | T | L | L | F | L | T | A | V | 152 |

| GTC | CAG | CGC | ATC | ACC | GTG | CAC | GTC | ACC | CGC | AGG | CCG | GTC | CTC | TAC | TTC | CAC | ATC | CGC | 513 |
|---|---|---|---|---|---|---|---|---|---|---|---|---|---|---|---|---|---|---|---|
| V | Q | R | I | T | V | H | V | T | R | R | P | V | L | Y | F | H | I | R | 171 |

| TGG | GGC | TTC | TCC | AAG | CAG | GTG | GTG | GCC | ATC | GTC | CAT | GCC | GTG | CTC | CTT | GGG | TTT | GTC | 570 |
|---|---|---|---|---|---|---|---|---|---|---|---|---|---|---|---|---|---|---|---|
| W | G | F | S | K | Q | V | V | A | I | V | H | A | V | L | L | G | F | V | 190 |

| ACT | GTG | TCC | TGC | TTC | TTC | TTC | ATC | CCG | GCC | GCT | GTC | TTC | TCA | GTC | CTG | GAG | GAT | GAC | 627 |
|---|---|---|---|---|---|---|---|---|---|---|---|---|---|---|---|---|---|---|---|
| T | V | S | C | F | F | F | I | P | A | A | V | F | S | V | L | E | D | D | 209 |

FIG. 1B

```
TGG AAC TTC CTG GAA TCC TTT TAT TTT TGT TTT ATT TCC CTG AGC ACC ATT GGC CTG    684
 W   N   F   L   E   S   F   Y   F   C   F   I   S   L   S   T   I   G   L    228

GGG GAT TAT GTG CCT GGG GAA GGC TAC AAT CAA AAA TTC AGA GAG CTC TAT AAG ATT    741
 G   D   Y   V   P   G   E   G   Y   N   Q   K   F   R   E   L   Y   K   I    247

GGG ATC ACG TGT TAC CTG CTA CTT GGC CTT ATT GCC ATG TTG GTA GTT CTG GAA ACC    798
 G   I   T   C   Y   L   L   L   G   L   I   A   M   L   V   V   L   E   T    266

TTC TGT GAA CTC CAT GAG CTG AAA AAA TTC AGA AAA ATG TTC TAT GTG AAG AAG GAC    855
 F   C   E   L   H   E   L   K   K   F   R   K   M   F   Y   V   K   K   D    285

AAG GAC GAG GAT CAG GTG CAC ATC ATA GAG CAT GAC CAA CTG TCC TTC TCC TCG ATC    912
 K   D   E   D   Q   V   H   I   I   E   H   D   Q   L   S   F   S   S   I    304

ACA GAC CAG GCA GCT GGC ATG AAA GAG GAC CAG AAG CAA AAT GAG CCT TTT GTG GCC    969
 T   D   Q   A   A   G   M   K   E   D   Q   K   Q   N   E   P   F   V   A    323

ACC CAG TCA TCT GCC TGC GTG GAT GGC CCT GCA AAC CAT TGA gcgtaggatttgttgcatt   1030
 T   Q   S   S   A   C   V   D   G   P   A   N   H   *                        337
atgctagagcaccagggtcagggtgcaaggaagaggcttaagtatgttcatttttatcagaatgcaaaagcgaaaa   1106
ttatgtcactttaagaaatagctactgtttgcaatgtcttattaaaaaacaacaaaaaaagacacatggaacaaag   1182
aagctgtgaccccagcaggatgtctaatatgtgaggaaatgagatgtccacctaaaattcatatgtgacaaaatta   1258
tctcgaccttacataggaggagaatacttgaagcagtatgctgctgtggttagaagcagattttatacttttaact   1334
ggaaactttggggtttgcatttagatcatttagctgatggctaaatagcaaaatttatatttagaagcaaaaaaaa   1410
aaagcatagagatgtgttttataaataggtttatgtgtactggtttgcatgtacccacccaaaatgattattttg    1486
gagaatctaagtcaaactcactatttataatgcataggtaaccattaactatgtacatataaagtataaatatgtt   1562
tatattctgtacatatggtttaggtcaccagatcctagtgtagttctgaaactaagactatagatattttgtttct   1638
tttgatttctctttatactaaagaatccagagttgctacaataaaataaggggaataataaaaaaaaaaaaaaa    1712
```

FIG. 1B

|          | 1                          | 14            | 27       |
|----------|----------------------------|---------------|----------|
| TWIK-1 P1 | FTSALFFASTVLSTTGYGHTVPLSDGG |
| TWIK-1 P2 | FLESFYFCFISLSTIGLGDYVPGEGYN |
| TOK1 P2  | YFNCIYFCFLCLLTIGYGDYAPRTGAG |
| TOK1 P1  | YGNALYFCTVSLLTVGLGDILPKSVGA |
| Slo      | YWTCVYFLIVTMSTVGYGDVYCETVLG |
| Shaker   | IPDAFWWAVVTMTTVGYGDMTPVGFWG |
| Shab     | IPEAFWWAGITMTTVGYGDICPTTALG |
| Shal     | IPAAFWYTIVTMTTLGYGDMVPETIAG |
| Shaw     | IPLGLWWALVTMTTVGYGDMAPKTYIG |
| KAT1     | YVTALYWSITTLTTTGYGDFHAENPRE |
| AKT1     | YVTSMYWSITTLTTVGYGDIHPVNTKE |
| eag      | YVTALYFTMTCMTSVGFGNVAAETDNE |
| ROMK1    | MTSAFLFSLETQVTIGYGFRFVTEQCA |
| IRK1     | FTAAFLFSIETQTTIGYGFRCVTDECP |
| GIRK1    | FPSAFLFFIETEATIGYGYRYITDKCP |

FIG. 2A

```
TWIK-1    1  MLQSLAGSSCVREVE------RHRSAWCF--GF----------LVLGY
f17c8     1  MYTDEGEYSGDTDHGGSTMQKMSPNTRQNFRQNVNVVVCLSAAITL--
M110-2    1  MTVSMEENSKIQMLSATSKDKKVATDRSLLNKYHLGPLALHTGLVLSC

TWIK-1   31  LEYLVFGAVVFSSVELPYEDLLRQE-----LRKLKRRFLEEHEC---L
f17c8    47  LVFNLIGAGIF---------------------------YLAETQNSSES
M110-2   49  VTYALGGAYLFLSIEHP-EELKRREKAIREFQDLKQQFMGNITSGIEN

TWIK-1   71  SEQQLEQFLGRVL-------EASNYGVSVLSNASGNWNW--DFTSALF
f17c8    69  LNENSEV--SKCLHNLPIGGKITAEMKSKLGKCLTKSSRIDGFGKAIF
M110-2   96  SEQSIEIYTKKLILMLEDAHNAHAFEYFFLNHEIPKDMW--TFSSALV

P1
TWIK-1  110  FASTVLSTTGYGHTVPLSDGGKAFCII-YSVIGIPFTLLFLTAVVQRI
f17c8   115  FSWTLYSTVGYGSLYPHSTLGRYLTIF-YSLLMIPVFIAFKFEFGTFL
M110-2  142  FTTTTVIPVGYGYIEPVSAYGR-MCLIAYALLGIPLTLVTMADTGKFA

TWIK-1  157  TVH---VTRRPVL-----YFHIRWGFSKQVVAIVHAVLLGFVTVSCFF
f17c8   162  AHFLVVVSNRTRLAVKKAYYKLS-QNPENAETPSNSLQHDYLIFLSSL
M110-2  189  AQL---VTR--------------W-FGDNNMAIPAAIFV------CLL

P2
TWIK-1  197  FI-PAAVFS---VL--EDDWNFLESFYFCFISLSTIGLGDYVPGEGYN
f17c8   209  LLCSESLLSSSALFSSIENISYLSSVYFGIITMFLIGIGDIVPTN---
M110-2  213  FAYPLVVGF---ILCSTSNITYLDSVYFSLTSIFTIGFGDLTP-----

TWIK-1  239  QKFRELYKIGITCYLLGLIAMLVVLETFC----ELHELKKFR-----
f17c8   254  -------LVWFSGYCMLFLISDVLSNQIFYFCQARVRYFFHILARKIL
M110-2  253  ----DMNVIHMVLFLAVGVILVTITLDIVA---AEMIDRVHYMGRHVG

TWIK-1  278  -------KMFYVKKDKDEDQVHIIEHDQL----SFSSITDQAAGMKED
f17c8   295  LLRE-EDDGFQLETTVSLQHIPIINSQCMPSL----VLDCEKEELDND
M110-2  294  KAKELAGKMFQLAQSLNMKQGLVSGVGQLHALARFGMLVGREEVDKTQ

TWIK-1  315  QKQNEPFVAT---------------QSSACVDGPANH----
f17c8   338  EKLISSLTST-------------------------------
M110-2  342  EDGIIAFSPDVMDGLEFMDTLSIYSRRSRRSAENSARNLFLS
```

FIG. 2B

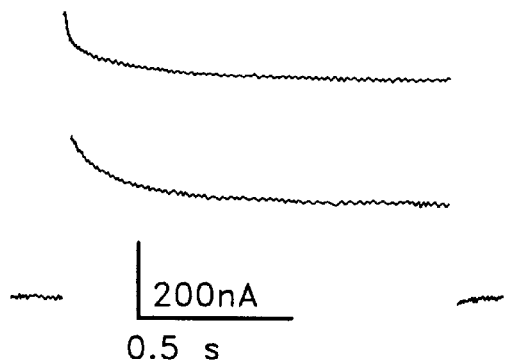
FIG. 7a
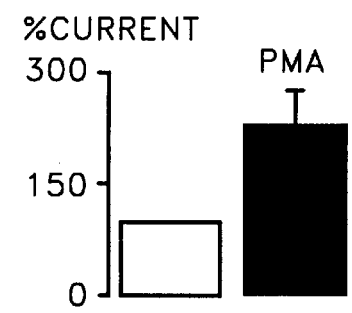
FIG. 7b
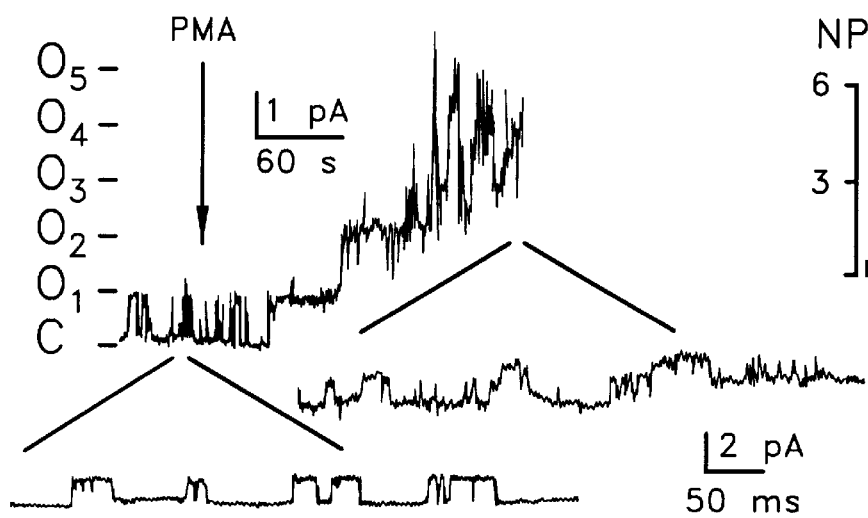
FIG. 7c
FIG. 7d

FAMILY OF MAMMALIAN POTASSIUM CHANNELS, THEIR CLONING AND THEIR USE ESPECIALLY FOR THE SCREENING OF DRUGS The present invention relates to a new family of potassium channels. More specifically, the invention relates to the cloning of a human potassium channel that constitutes the first member of a new functional and structural group of potassium channels. The abundance of this channel and its presence in a large number of tissues are such as to confer on it a fundamental role in the transport of potassium in a large number of types of cells.

BACKGROUND OF THE INVENTION

Potassium channels are ubiquitous in eukaryote and prokaryote cells. Their exceptional functional diversity make them ideal candidates for a large number of biological processes in living cells (Rudy, B., 1988, *Neurosciences*, 25, 729–749; Hille, B., 1992, *"Ionic Channels of Excitable Membrane"*, 2nd edition, Sinauer, Sunderland, Mass.). In excitable cells, the $K^+$ channels define the form of the action potentials and the frequency of the electric activity, and play a major role in neuronal integration, muscle contraction or hormonal secretion. In nonexcitable cells, their expression appears to be correlated with specific stages of the development of the cell (Barres, B. A. et al., 1990, *Annu. Rev. Neurosci.*, 13, 441–474). In most cells, specific types of $K^+$ channels play a vital role in determining the electrical potential of the membrane at rest by regulating the membrane permeability to $K^+$ ions. These channels exhibit the characteristic of being instantaneous and open in a large range of membrane potentials.

Recent cloning studies have resulted in the identification of a large number of subunits capable of forming potassium channels (Betz, H., 1990, *Biochemistry*, 29, 3591–3599; Pongs, O., 1992, *Physiol. Rev.*, 72, S69–88; Salkoff, L. et al., 1992, *Trends Neurosci.*, 15, 161–166; Jan, L. Y. and Y. N. Jan, 1994, *Nature*, 371, 199–122; Doupnik, C. A. et al., 1995, *Curr. Opin. Neurobiol.*, 5, 268–277) which could be regulated by other types of subunits (Aldrich, R. W., 1994, *Curr. Biol.*, 4, 839–840; Isom, L. L. et al., 1994, *Neuron*, 12, 1183–1194; Rettig, J. et al., 1994, *Nature*, 369, 289–294; Attali, B. et al., 1995, *Proc. Natl. Acad. Sci. USA*, 92, 6092–6096).

The subunits of the voltage-dependent $K^+$ channels activated by depolarization (Kv families) and the calcium-dependent $K^+$ channels exhibit six hydrophobic transmembranal domains, one of which (S4) contains repeated positive charges which confer on these channels their sensitivity to voltage and, consequently, in their functional outward rectification (Logothetis, D. E. et al., 1992, *Neuron*, 8, 531–540; Bezanilla, F. and Stefani, E., 1994, *Annu. Rev. Biophys. Biomol. Struct.*, 23, 819–846).

The $K^+$ channels with inward rectification (Kir families) have only two transmembranal domains. They do not have the S4 segment and the inward rectification results from a voltage-dependent blockade by cytoplasmic magnesium (Matsuda, H., 1991, *Annu. Rev. Physiol.*, 53, 289–298; Lu, Z. and Mackinnon, R., 1994, *Nature*, 371, 243–246; Nichols, C. G. et al., 1994, *J. Physiol. London*, 476, 399–409).

A common structural unit, called the P domain, is found in both groups, and constitutes an essential element of the structure of the $K^+$-permeable pore. The presence of this unit in a membrane protein is considered to be the signature of the structure of a $K^+$ channel (Pongs, O., 1993, *J. Membrane Biol.*, 136, 1–8; Heginbotham, L. et al., 1994, *Biophys. J.*, 66, 1061–1067; Mackinnon, R., 1995, *Neuron*, 14, 889–892; Pascual, J. M. et al., 1995, *Neuron*, 14, 1055–1063).

SUMMARY OF THE INVENTION

The present invention is based on the cloning of a $K^+$ channel which is the first member of a new structural and functional group of potassium channels. This new $K^+$ channel has a novel molecular architecture with four transmembranal segments and two P domains. From a functional point of view, this channel is remarkable in that it exhibits weak inward rectification properties. This new channel is referred to below as TWIK-1 following the English-language term "Tandem of P domains in a Weak Inward rectifying $K^+$ channel". Its abundance and its presence in a large number of tissues are such as to confer on it a fundamental role in the transport of potassium in a large number of types of cells.

The discovery of this new family of potassium channels and the cloning of a member of this family provides, notably, new means for screening drugs capable of modulating the activity of these new potassium channels and thus of preventing or treating the diseases in which these channels are involved.

The research activities that led to the cloning of the TWIK-1 channel were carried out in the manner described below with reference to the attached sequences and drawings in which:

SEQ ID NO: 1 represents the nucleotide sequence of the cDNA of TWIK-1 and the amino acid sequences of the coding sequence.

SEQ ID NO: 2 represents the amino acid sequence of the TWIK-1 protein.

DESCRIPTION OF THE FIGURES

FIG. 2 represents the sequence alignments. (a): alignment of the P domains of TWIK-1, TOC/YORK and other representative $K^+$ channel families; the identical and conserved residues are circled in black and in gray, respectively. (b): alignment of TWIK-1 with potential homologues of *C. elegans;* the sequences M110.2 and F17C8.5 were deduced from the gene sequences (respective access numbers Z49968 and Z35719); the computerized splicing of the other genomic sequences of *C. elegans* (respective access numbers Z49889, P34411 and Z22180) is not sufficiently precise to allow their perfect alignment and is therefore not shown.

FIG. 7 shows the activation of the TWIK-1 channels by PMA, activator of protein kinase C. (a): perfusion of PMA (30 nM) for 10 minutes increases the TWIK-1 current (top tracing) induced by a depolarization phase at +30 mV starting at HP=−80 mV, control current (top tracing). (b): graph (n=5) showing the activation effect of PMA on the TWIK-1 currents. (c and d): attached patch configuration under symmetrical K$^+$ concentration conditions maintained at +60 mV; (c): course over time of the effect of 30 nM of PMA on the single channel activities; the recordings of the channel activity were performed with a rapid scanning before and after the application of PMA; (d): bar graph (n=5) showing the activation effect of PMA on NP$_o$.

DETAILED DESCRIPTION OF THE INVENTION

Figure 1A:
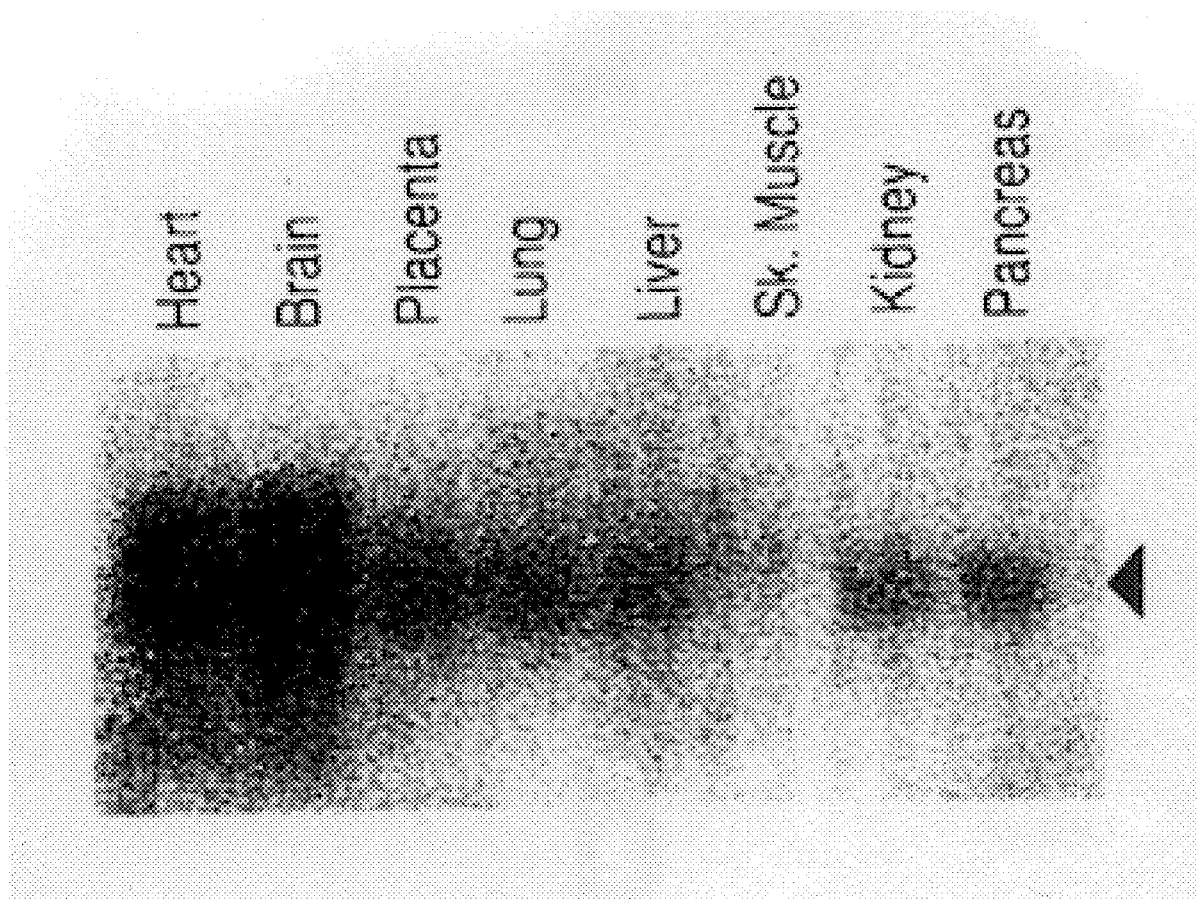
FIG. 1 represents the Northern blot analysis, the nucleotide sequences and the deduced amino acid sequence, as well as the hydrophobicity profile of TWIK-1. (a): expression of TWIK-1 mRNA in human tissues; each track contains 5 µg of poly(A)$^+$; the autoradiograph was exposed for 24 hours. (b) cDNA sequence of TWIK-1 and the amino acid sequences of the coding sequence. The supposed transmembranal segments are circled and the P domains are underlined; o represents a potential glycosylation site and ■ represents the threonine residue in the consensus recognition site of protein kinase C. (c): the hydrophobicity analysis and the topology of TWIK-1 deduced from it; the hydrophobicity values were calculated according to the method of Kyte and Doolittle (window size of 11 amino acids) and are presented in relation to the position of the amino acid; the shaded hydrophobic peaks correspond to the transmembranal segments.

The P domains of K$^+$ channels were used to determine the corresponding sequences in the GenBank data base by means of the BLAST sequence alignment program (Altschul, S. F. et al., 1990, *J. Mol. Biol.*, 215, 403–410). There was thus identified a 298 pb human Tag expressed sequence (EST, HSC3AH031), the deduced amino acid sequence of which includes a nonconventional "P-like" domain sequence: GLG in place of GYG as shown in FIG. 2a. It was then envisaged that this EST sequence was a partial copy of a mRNA coding a new type of K$^+$ channel subunit. A DNA probe was prepared from this sequence in order to carry out hybridization with a Northern blot (Clontech) of multiple human tissues. A 1.9 kb transcript was thereby found in abundance, as shown in FIG. 1a, in the heart and the brain and, at lower levels, in the placenta, the lung, the liver and the kidney. The DNA probe was used to screen a bank of kidney cDNA and four independent clones were obtained. The cDNA inserts of 1.8 to 1.9 kb of these clones all have the same open reading frame (ORF) containing a regio identical to the 298 pb sequence of HSC3AH031 and differing solely in the length of their noncoding 5' sequences.

Primary Structure of TWIK-1

The following characteristics were demonstrated:

The sequences of the cDNA clones contain an ORF of 1011 nucleotides coding for a polypeptide of 336 amino acids shown in FIG. 1b.

This protein has two P domains.

Other than the P domains, no significant alignment was seen between TWIK-1 and a K$^+$ channel recently cloned in yeast and which also has two P domains (Ketchum, K. A. et al., 1995, *Nature*, 376, 690–695).

Figure 1C:
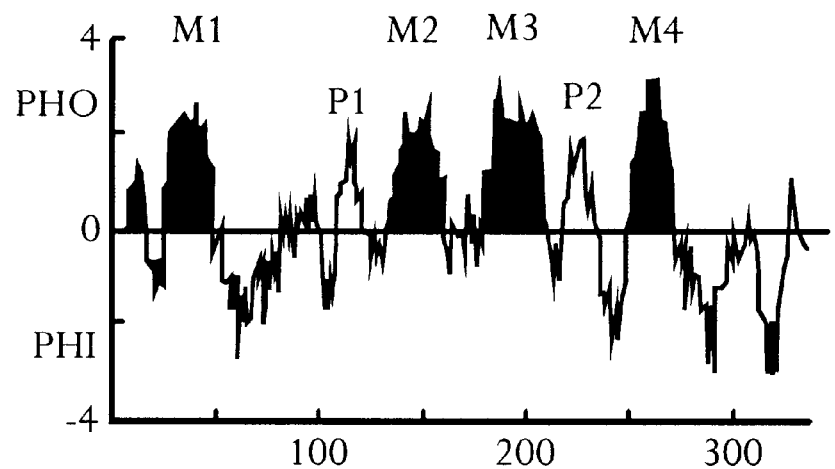
Figure 1C:
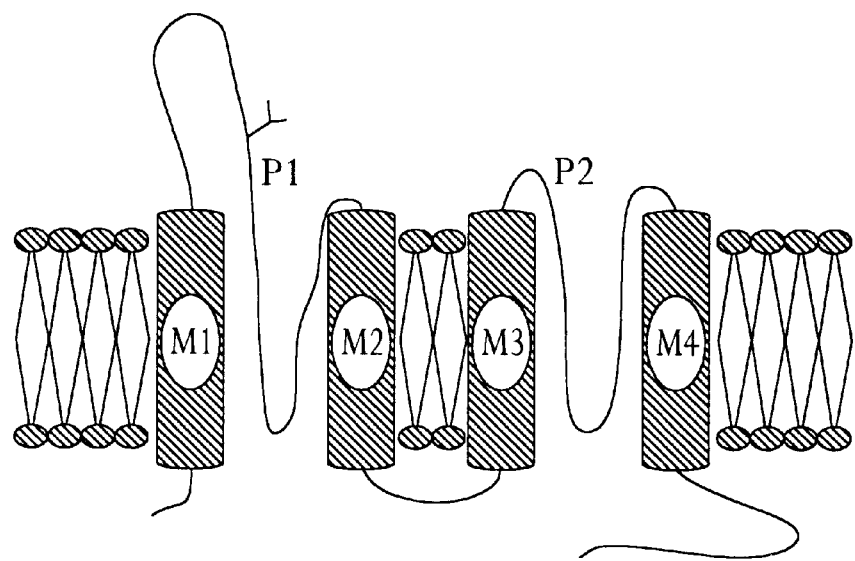

Analysis of the hydrophobicity of TWIK-1, shown in FIG. 1c, reveals the presence of four transmembranal domains, designated T1 to T4.

By placing the NH2 end on the cytoplasmic surface, in accordance with the absence of signal peptide, one obtains the topology model shown in FIG. 1c.

In this model, the two P domains are inserted in the membrane from the exterior in accordance with the known orientation of these loops in the K$^+$ channels.

In addition, the general structural unit of TWIK-1 is similar to the unit that one would obtain by making a tandem of two classical subunits rectifying the entry of a potassium channel. Like a classical inward rectifier, TWIK-1 does not exhibit the highly conserved segment S4 which is responsible for the sensitivity to the membrane potential of the inward rectification of the K$^+$ channels of the Kv family.

A nonusual large loop of 59 amino acids is present between M1 and P1, such as to extend the length of the linker M1-P1 of the extracellular side of the membrane.

A potential site of N-glycosylation is present in this loop.

Three consensus sites of phosphorylation are present at the N-terminal (Ser 19 for calcium calmodulin kinase II) and C-terminal (Ser 303 for casein kinase II) ends of the cytoplasmic domains, and in the M2-M3 linker (Thr161 for protein kinase II).

The alignment of the P domains of an important group of $K^+$ channels is presented in FIG. 2a. It shows that the regions constituting the pore selective for $K^+$ are well conserved including the G residues in position 16 and 18 and three other residues indicating practically exclusively conservative changes in positions 7, 14 and 17. It is of interest to note that a leucine residue is present in the place of a tyrosine conserved in position 18 in the P2 domain of TWIK-1, or of a phenylalanine in position 17 of the P domain of the $K^+$ channel of type eag.

The homologues of TWIK-1

Comparison of the complete sequence of TWIK-1 with the sequences of the Genbank data base allowed identification of at least five genes of *Caenorhabditis elegans* which had been characterized in the context of the Nematode Sequencing project, and which potentially code for structural homologues of TWIK-1. The alignment of two of these homologues with TWIK-1 is shown in FIG. 2b. The homologies of total sequences between the deduced proteins of *C. elegans* and TWIK-1 are circa 55 to 60% and circa 25 to 28% of identity. The homologies among sequences of *C. elegans* are not higher.

Functional expression of TWIK-1

Figure 3C:
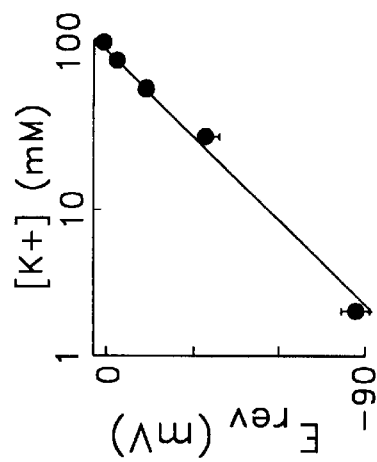
FIG. 3 shows the biophysical and pharmacological properties of $K^+$ currents recorded by the imposed voltage technique on Xenope oocytes that had received an injection of TWIK-1 cRNA; (a): the oocyte was maintained at a holding potential (HP) of −80 mV and the currents were recorded at the end of 1-s voltage jumps from −120 to +60 mV in 20 mV increments. (b): regular current-voltage relationship using the same technique as in (a). (c): potential reversal of the TWIK-1 currents ($E_{rev}$) as a function of the external K$^+$ concentration. (d) current tracings linked to +30 mV depolarizations starting at a holding potential (HP) of −80 mV in the absence (top tracing) and in the presence (bottom tracing) of 1 mM of Ba$^{2+}$. (e): blocking effect of 100 μM of quinine, same protocol as in (d). (f) dose-response relationship of the blocking of the TWIK-1 currents by quinine.
Figure 3B:
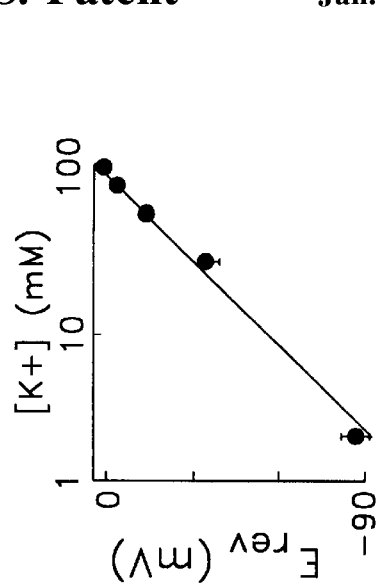
Figure 3A:
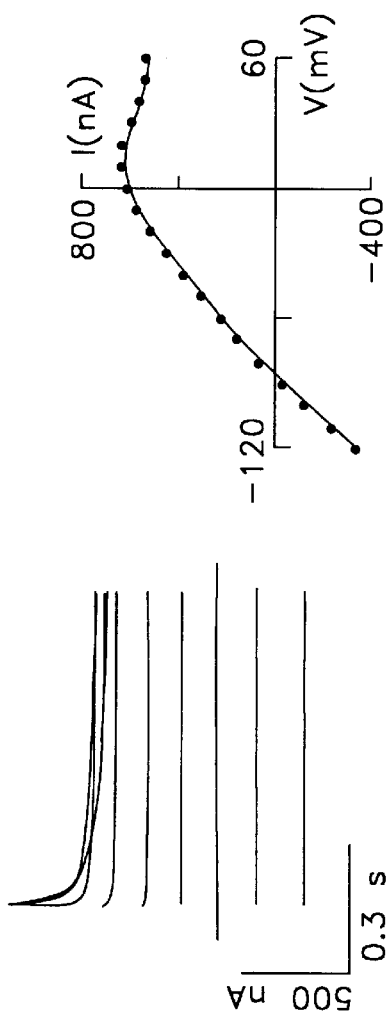
Figure 3F:
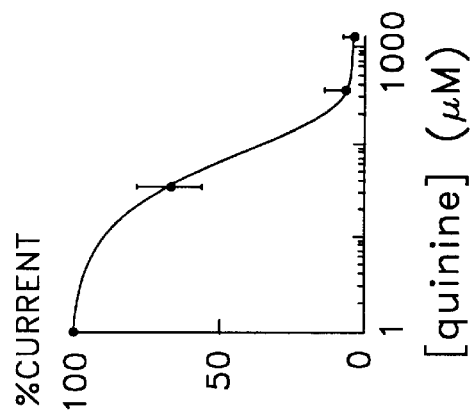
Figure 3E:
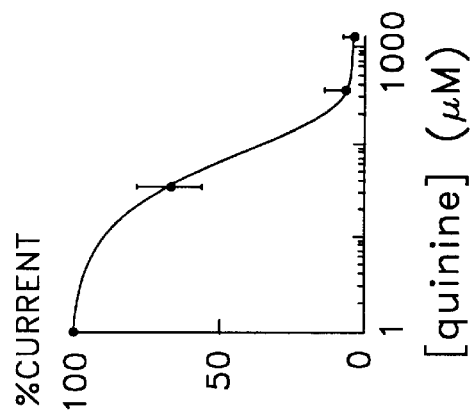
Figure 3D:
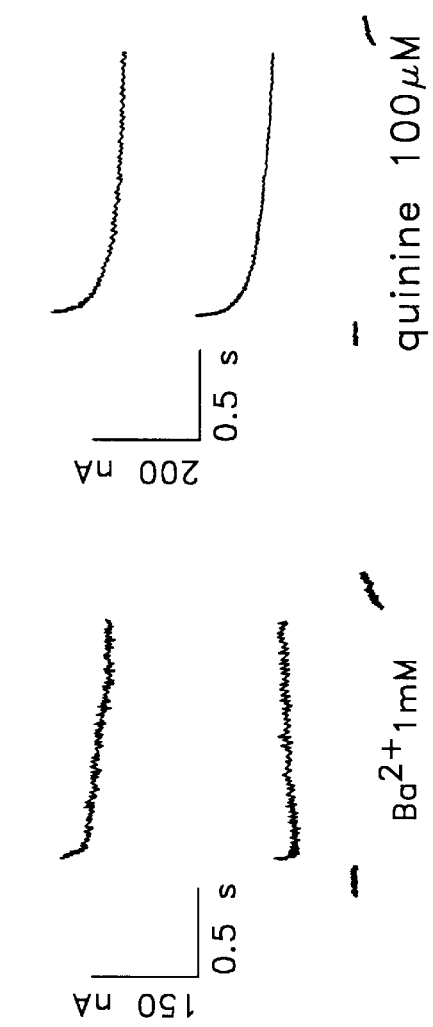

For the functional study, the coding sequence of TWIK-1 was inserted between the noncoding sequences 5' and 3' of Xenopus globin in the vector pEXO (Lingueglia, E. et al., 1993, *J. Biol. Chem.*, 269, 13736–13739). A complementary RNA (cRNA) was transcribed of this construction and injected in the oocytes of *X. laevis*. A noninactivating current, free from noninjected cells, was measured by the imposed voltage technique, as shown in FIG. 3a. Kinetic activation of the current is usually instantaneous and cannot be resolved because it is masked by the capacitive discharge of the current recorded at the beginning of the impulse. The current-voltage relationship is linear above 0 mV and then saturates for a stronger depolarization of the membrane, as shown in FIG. 3b. TWIK-1 is therefore $K^+$ selective. In the case of a replacement of the external $K^+$ by $Na^+$ or N-methyl-D-gluconate, the reversal of the potential of the currents follows the $K^+$ equilibrium potential ($E_K$), as shown in FIG. 3c. In addition, a change by 10 in the concentration $[(K)]_o$ leads to a change of 56±2 mV in the inversion value of the potential, in accordance with Nernst's equation.

As shown in FIG. 3, the $K^+$ currents of TWIK-1 are inhibited by $Ba^{2+}$ (FIG. 3d) with an $IC_{50}$ value of 100 $\mu$M, by quinine (FIGS. 3e and 3f) and by quinidine (not shown) with respective $IC_{50}$ values of 50 and 95 $\mu$M. The TWIK-1 currents are slightly sensitive to TEA and to the class III antiarrhythmic agent tedisamil (30% inhibition for each, at 20 mM and 100 $\mu$M, respectively). Less than 10% inhibition was seen after application of 4-aminopyridine (1 mM), apamin (0.3 $\mu$M), charybdotoxine (3 nM), dedrotoxine (0.1 $\mu$M), clofilium (30 $\mu$M), amiodarone (100 $\mu$M) and glibenclamide (30 $\mu$M). The TWIK-1 channel is not sensitive to the $K^+$ channel openers cromakaline (100 $\mu$M) and pinacidil (100 $\mu$M).

Figure 4A:
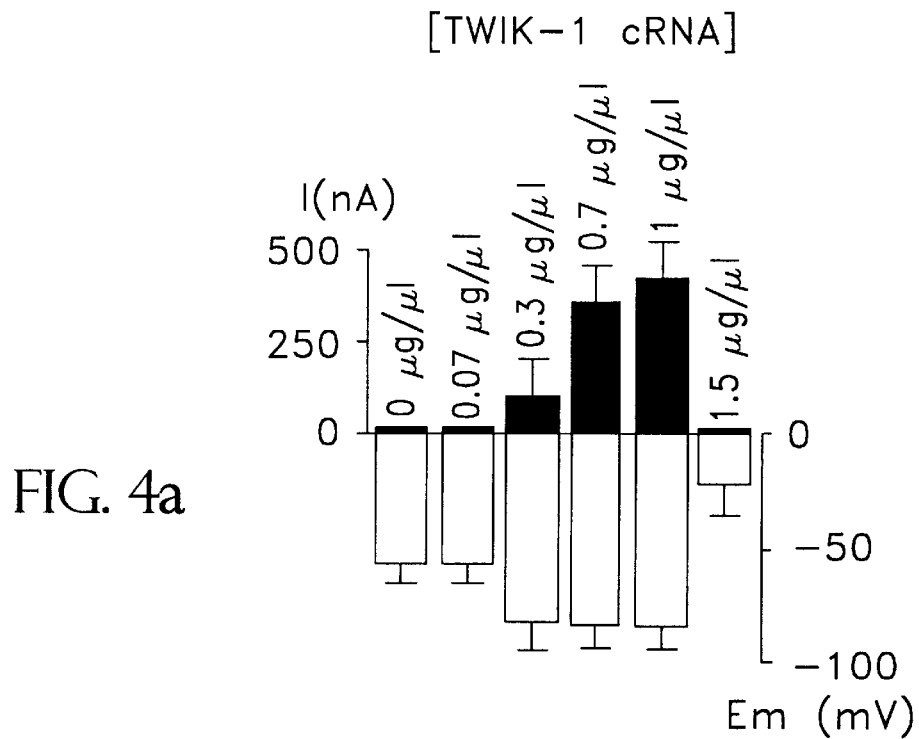
FIG. 4 shows the influence of the expression of TWIK-1 on the membrane potential. (a): dose-response relationships of the cRNA; top row=equilibrium state of the outward currents measured at +30 mV; bottom row=membrane potentials associated with the resting state. (b): effect of 100 μM of quinine on the membrane potential of an oocyte which did not receive an injection (left tracing) and that of an oocyte that received 20 ng of TWIK-1 cRNA. (c): statistical evaluation of the depolarizing effects of 100 μM of quinine on oocytes that did not receive injections (left bars) and on oocytes that received injections of 20 ng of TWIK-1 cRNA (right bars); control (unfilled bar), +quinine (solid bars); each bar represents the mean±SD of 5 oocytes.
Figure 4B:
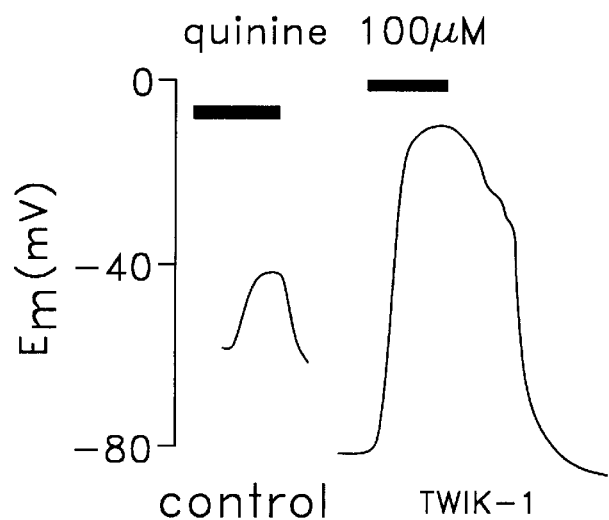
Figure 4C:
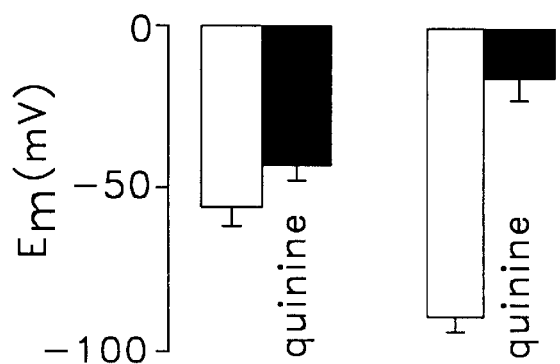

FIG. 4 shows the effect of increasing the doses of injected TWIK-1 cRNA on the independent expression of the time of the $K^+$ currents and on the resting state of the membrane potential ($E_m$). As soon as the current appears, the oocytes become increasingly polarized, reaching a value of $E_m$ close to $E_K$. The amplitude of the TWIK-1 current reaches values of 0.6 to 0.8 $\mu$M with the injection of 20 ng per oocyte. Higher doses of TWIK-1 cRNA are toxic, leading to a reduction in expression. In oocytes that received 20 ng of cRNA, quinine is the best blocker of TWIK-1, inducing a noteworthy reversible depolarization (73±6 mV, n=5) as shown in FIGS. 4b and 4c.

The Unitary Properties of the TWIK-1 Channel

Figures 5A, 5B:
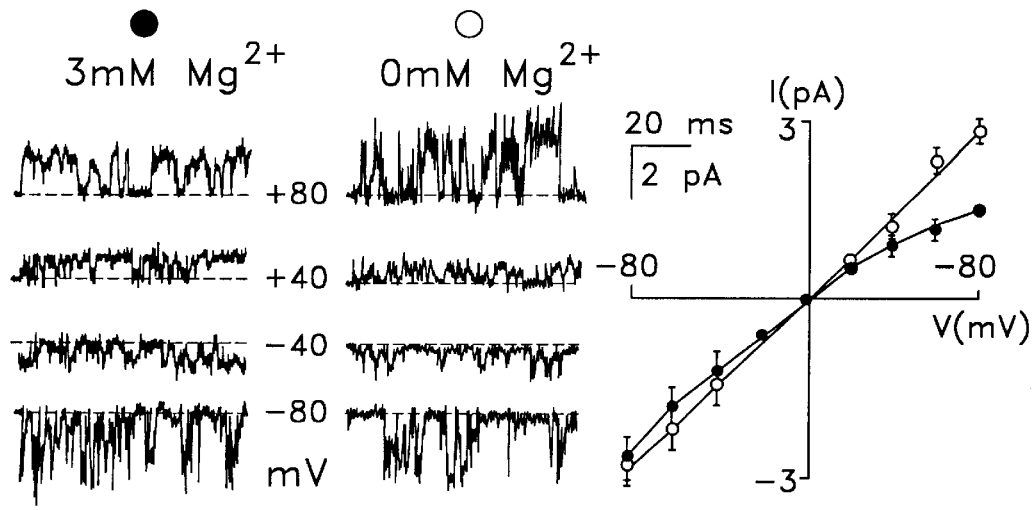
FIG. 5 shows the properties of the single TWIK-1 channel. (a): current tracings recording in the input-output configuration to the membrane potentials indicated in the absence (m) or in the presence (·) of internal M$^{2+}$ (3 mM) and in symmetry with 140 mM of K$^+$. (b): mean of curves I–V (n=10). (c and d): open time of distribution obtained at +80 mV (top histograms) and at −80 mV (bottom histograms) in the presence of 3 mM Mg$^{2+}$ (c) or in the absence of Mg$^{2+}$ (d).
Figures 5C, 5D:
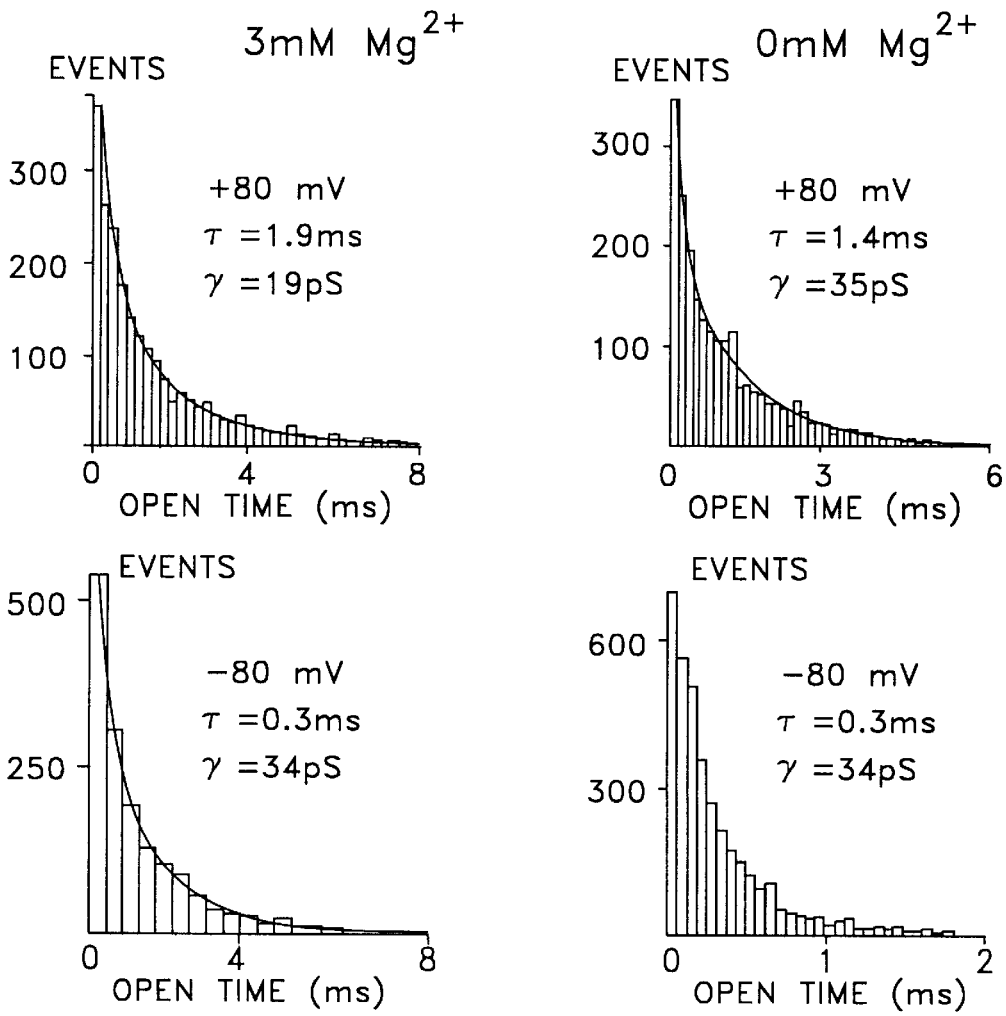

Single channel current recordings, shown in FIG. 5, in an inside-out patch configuration or in a whole cell configuration show that the TWIK-1 channels assure the passage of influx or exit currents as a function, respectively, of a depolarization or a hyperpolarization (FIG. 5a). The current-voltage relationship of the single channel, shown in FIG. 5b, shows a barely accentuated inward rectification in the presence of 3 mM (FIG. 5) and 10 mM (not shown) of $Mg^{2+}$ on the cytoplasmic side. As shown in FIG. 5b, this rectification disappears in the absence of internal $M^{2+}$. With 3 mM of internal $Mg^{2+}$, the mean duration of opening at +80 mV is 1.9 ms and the unitary conductance is 19±1 pS (FIG. 5c). At −80 mV, the channels are oscillating with a mean duration of opening of 0.3 ms, and a conductance value increasing to 34±pS. The withdrawal of the internal $Mg^{2+}$ ions does not influence the kinetic parameters under either polarized or depolarized conditions, but the unitary conductance measured at −80 mV reaches 35±4 pS. This apparent increase in conductance in the single channel suggests that it is the extremely rapid oscillation induced by $Mg^{2+}$ that results in an underestimation of the real value of conductance. The same properties were observed in the fixed cell configuration, showing that the channel behavior is not modified by the excision of the patch. The TWIK-1 channels in the excised patches do not discharge and do not appear to be deficient in intracellular constituents. In contrast to numerous channels which require the presence of ATP for their activity in the excised patch configuration, ATP is not required for the expression of TWIK-1. In addition, perfusion of the patch with a solution containing 10 mM of ATP does not induce any effect on the activity of the TWIK-1 channel.

The Activity Regulation Properties of the TWIK-1 Channel

The intracellular pH ($Ph_i$) is involved in the control of numerous cellular processes, and in cells such as the hepatic cells, the change in $Ph_i$ regulates the membrane potential (Bear, C. E. et al., 1988, *Biochim. Biophys. Acta*, 944, 113–120).

Intracellular acidification of the oocytes was produced using two methods:
  superfusion with a solution enriched in $CO_2$ which produces acidification by a mechanism involving the bicarbonate transport system (Guillemare, E. et al., 1995, *Mol. Pharmacol.*, 47, 588–594);
  treatment with dinitrophenol (DNP), which is a metabolic inhibitor that decouples the $H^+$ gradient in mitochondria and induces internal acidity (Pedersen, P. L. and Carafoli, E., 1987, *Trends Biol. Sci.*, 12, 146–189).

Figure 6A:
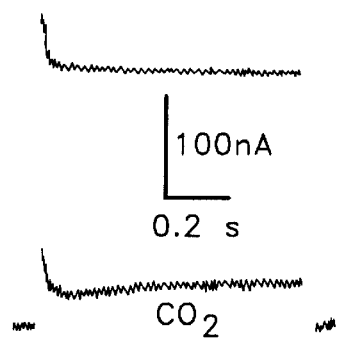
FIG. 6 shows the blocking of the TWIK-1 channels by the internal pH. (a and b): blocking effect of the internal acidification on the TWIK-1 currents, induced by perfusion of CO$_2$; (a) tracings of superimposed currents induced by a depolarization phase at −30 mV starting at HP=−80 mV, control (top tracing), effect when equilibrium is reached in the presence of CO$_2$ (bottom tracing); (b): graph (n=5) showing the almost complete blockade of the TWIK-1 currents induced by CO$_2$; (c and d): internal acidification induced by the application of DNP (1 mM). (c): same protocol as in (a), control (top tracing) and after 5 minutes of application of DNP (bottom tracing); (d): graph (n=4) indicating the percentage of TWIK-1 current remaining after treatment with DNP. (e and f): imposed voltage (method: attached patch) under symmetrical conditions of K$^+$ concentration (140 mM) maintained at +80 mV. (e) course over time of the effect of 1 mM of DNP (marked with arrow) on the activities of the single TWIK-1 channel. (f): graph (n=4) showing the effect of DNP on the mean probability of opening NP$_o$ calculated during 1 minute of recording starting at the equilibrium state. (g): activities measured in the "inside-out-patch" state at 80 mV at different internal pH values. Bar graph (n=10) of NP$_o$ in relation to the internal pH.
Figure 6B:
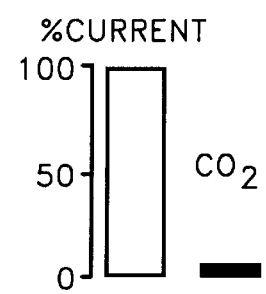
Figure 6C:
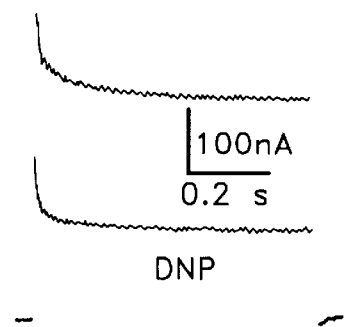
Figure 6D:
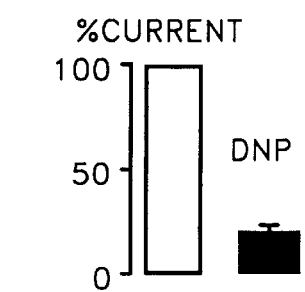
Figure 6E:
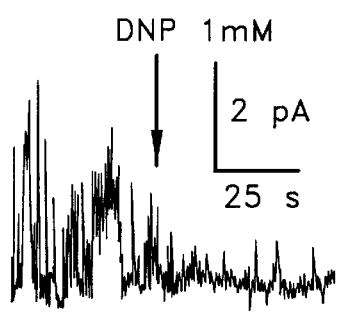
Figure 6F:
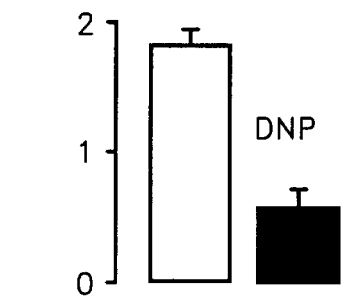
Figure 6G:
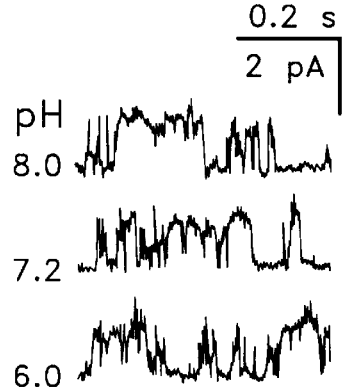
Figure 6H:
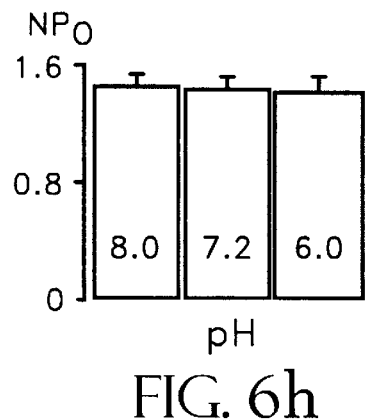

Both of these experimental methods resulted in a significant reduction in the TWIK-1 currents, greater than 95% in the case of $CO_2$ and 80% in the case of DNP of the control amplitude values, as shown in FIGS. 6a to 6d. The inhibition induced by DNP on the activity of the single $K^+$ channel was again observed under the attached patch conditions, as shown in FIGS. 6e to 6f. However, after excision of the patch, the activity of the channel became insensitive to the acidification of the internal solution produced either by modifying the $Na_2HPO_4/NaH_2PO_4$ buffer ratio (FIGS. 6g and 6h) or by bubbling of $CO_2$ (not shown). Thus, the effect of the pH value on the activity of the TWIK-1 channel is probably indirect.

Phosphorylation or dephosphorylation of specific amino acid residues is an important mechanism of regulation of the ionic channels (Levitan, I. B., 1994, *Annu. Rev. Physiol.*, 56, 193–212). As shown in FIG. 7, activation of protein kinase C by phorbol-12 myristate acetate (PMA, 30 nM) increases the TWIK-1 currents. The inactive phorbol ester 4α-phorbol-12, 13 didecanoate (PDA, 1 µM) has no effect. In an attached patch which initially expressed solely a single channel, application of PMA . . . the presence of at least five channels (FIGS. 7c and 7d). This experiment shows that at least four channels are silently present in the patch before the application of PMA. Since the TWIK-1 sequence contains a consensus phosphorylation site for protein kinase C (PKC), located at the level of the threonine in position 161 (FIG. 1b), the effect of PMA suggests regulation under the control of PKC. However, the mutation of the threonine 161 into alanine leads to a muted channel which remains functional and conserves the capacity to be activated by PMA.

Activation of protein kinase A by application of 8-Cl-AMPc (300 µM) or forskolin (10 µM) does not affect the activity of TWIK-1. Elevation of the cytoplasmic $Ca^{2+}$ concentration by application of A23187 (1 µM) which could be activated by $Ca^{2+}$-calmodulin kinase II and/or reveal the presence of a channel activated by the $Ca^{2+}$, is also without effect on the properties of the TWIK-1 channel.

Thus, the object of the present invention is an isolated, purified nucleic acid molecule that codes for a protein constituting a TWIK-1 potassium channel or exhibiting the properties and structure of the type of the TWIK-1 channel described above.

More specifically, the said nucleic acid molecule codes for the TWIK-1 protein, the amino acid sequence of which is represented in the attached sequence list as number SEQ ID NO:2, or a functionally equivalent derivative of this sequence. Such derivatives can be obtained by modifying and or suppressing one or more amino acid residues of this sequence, as long as this modification and/or suppression does not modify the functional properties of the TWIK-1 potassium channel of the resultant protein.

The sequence of a DNA molecule coding for this protein is more specifically the molecule coding for TWIK-1 represented in the attached sequence list as number SEQ ID NO:1.

The invention also relates to a vector containing a molecule of the aforementioned nucleic acid, as well as a procedure for production or expression in a cellular host of a protein constituting a TWIK-1 potassium channel or a channel of the same family as TWIK-1.

A procedure for production of a protein constituting a TWIK-1 potassium channel or exhibiting the properties and structure of the type of the TWIK-1 channel consists of:

transferring a nucleic acid molecule of the invention or a vector containing the said molecule into a cellular host, culturing the cellular host obtained in the preceding step under conditions enabling the production of potassium channels exhibiting the properties of TWIK-1, isolating by any suitable method the proteins constituting the potassium channels of the TWIK-1 family.

A procedure for expression of a TWIK-1 potassium channel or a potassium channel of the same family as TWIK-1 consist of:

transferring a nucleic acid molecule of the invention or a vector containing the said molecule into a cellular host, culturing the cellular host obtained in the preceding step under conditions enabling the expression of potassium channels of the TWIK-1 family.

The cellular host employed in the preceding procedures can be selected from among the prokaryotes or the eukaryotes, and notably from among the bacteria, the yeasts, mammal cells, plant cells or insect cells.

The vector used is selected in relation to the host into which it will be transferred; it can be any vector such as a plasmid.

The invention thus also relates to the transferred cells expressing the potassium channels exhibiting the properties and structure of the type of the TWIK-1 channel obtained in accordance with the preceding procedures.

The cells expressing TWIK-1 potassium channels or channels exhibiting the properties and structure of the type of the TWIK-1 channels obtained in accordance with the preceding procedures are useful for the screening of substances stances capable of modulating the activity of the TWIK-1 potassium channels. This screening is carried out by bringing into contact variable amounts of a substance to be tested with cells expressing the TWIK-1 channel or potassium channels exhibiting the properties and structure of the type of the TWIK-1 channels, then measuring, by any suitable means, the possible effects of said substance on the currents of the potassium channels of these channels.

This screening procedure makes it possible to identify drugs that useful in the treatment of diseases of the heart or of the nervous system. Diseases involving the potassium channels and thus likely to involve the channels of the TWIK-1 family are, for example, epilepsy, heart (arrhythmias) and vascular diseases, neurodegenerative diseases, especially those associated with ischemia or anoxia, the endocrine diseases associated with anomalies of hormone secretion, muscle diseases.

An isolated, purified nucleic acid molecule coding for a protein constituting a TWIK-1 potassium channel or a vector including this nucleic acid molecule or a cell expressing the TWIK-1 potassium channels, are also useful for the preparation of transgenetic animals. These can be animals supra-expressing the said channels, but especially so-called knock-out animals, i.e., animals presenting a deficiency of these channels; these transgenetic animals are prepared by methods known to the experts in the field, and enable the preparation of live models for studying animal diseases associated with the TWIK-1 channels.

The nucleic acid molecules of the invention or the cells transformed by said molecule can also be used in genetic therapy strategies for compensating for a deficiency in the potassium channels at the level of one or more tissues of a patient. The invention thus also relates to a medication containing nucleic acid molecules of the invention or cells transformed by said molecule for the treatment of disease involving the potassium channels.

In addition, the gene of the TWIK-1 channel has been located on chromosome 1 at position q42–q43. The chromosomal localization of this gene constitutes a determinant result for the identification of genetic diseases associated with this new family of potassium channels; thus, the knowledge of the structure of the TWIK-1 family of channels is such as to allow performance of a prenatal diagnosis of such diseases.

The present invention also has as its object a new family of $K^+$ channels, of which TWIK-1 is a member, which are present in most human tissues and especially abundant in the brain and the heart, and which exhibit the properties and structure of the type of those of the TWIK-1 channels described above. Thus it relates to an isolated, purified protein whose amino acid sequence is represented in the attached sequence list as number SEQ ID NO: 2, or a functionally equivalent derivative of this sequence.

Such derivatives can be obtained by modifying and/or suppressing one or more amino acid residues of this sequence or by segmenting this sequence, as long as this modification and/or suppression or deletion of a fragment does not modify the functional properties of the TWIK-1 type potassium channel of the resultant protein.

A protein constituting a TWIK-1 type potassium channel is useful for the manufacture of medications intended for the treatment or prevention of diseases involving dysfunction of the potassium channels.

Polyclonal or monoclonal antibodies directed against a protein constituting a TWIK-1 type potassium channel can be prepared by the conventional methods described in the literature.

These antibodies are useful for investigating the presence of potassium channels of the TWIK-1 family in different human or animal tissues, but they can also find applications in the therapeutic domain, due to their specificity, for the in vivo inhibition or activation of TWIK-1 type potassium channels.

Other advantages and characteristics of the invention will be made obvious from the examples below which are nonlimitative examples related to the cloning and expression of TWIK-1.

Identification of the HSC3AH031 EST Sequence and Analysis of the RNA

The P domains of the cloned channels were used to investigate homologues in the NCBI (National Center of Biotechnology) data bases using the sequence alignment program tBLASTn. Translation of an EST sequence (HSC3AH031, Genbank access number: F12504) presented a significant sequence similarity ($P=1.2\times10^{-3}$) with the second P domain of a yeast $K^+$ channel. This 298 pb sequence was originally obtained from a human brain cDNA bank in the context of the Genexpress cDNA program (Auffray, C. et al., 1995, C. R. Acad. Sci., III, Sci. Vie, 318, 263–272). A 255 pb DNA fragment corresponding to HSC3AH031 was amplified by PCR from cDNA derived from human brain poly(A)$^+$ and subcloned in pBluescript (Stratagene) to yield pBS-HSC3A.

For the RNA analysis, a Northern blot of multiple human tissues (Clontech) was screened with the pBS-HSCA insert tagged with $P^{32}$ in 50% formamide, 5×SSPE (0.9 M NaCl; 50 mM sodium phosphate; pH 7.4; 5 mM EDTA), 0.1% SDS, 5×Denhardts, 20 mM potassium phosphate, pH 6.5 and 250 µg of salmon sperm DNA denatured at 55° C. for 18 hours. The blots were washed to a final stringency of 0.1 SSC (3 M NaCl; 0.3 M sodium citrate; pH 7.0), 0.3% SDS at 65° C.

Isolation of the cDNA cloning TWIK-1

An oligo(dT) cDNA bank stemming from poly(A)$^+$ RNA isolated from human adult kidney was screened with the pBS-HSCA insert tagged with $P^{32}$. The filters were hybridized in 50% formamide, 5×SSC, 4×Denhardt, 0.1% SDS and 100 µg of salmon sperm DNA denatured at 50° C. for 18 hours. Four positive hybridization clones were isolated from circa $5\times10^5$ clones. The λZAPII phages containing the cDNA inserts were converted into cDNA plasmids (Stratagene). The DNA inserts were characterized by restriction enzyme analysis and by total or partial DNA sequencing on both strands using the dideoxy nucleotide method on an automated sequencer (Applied Biosystems 373A).

Mutations, cRNA Synthesis and Oocyte Injection

The TWIK-1 coding sequence was amplified using a low-error rate DNA polymerase (Pwo DNA pol, Boehringer) and subcloned in the plasmid pEXO so as to yield pEXO-TWIK-1. Mutations were performed using the whole plasmid pEXO-TWIK-1 with a highly reliable PCR extension kit (Boehringer) and two adjacent primers. One of these introduced a punctiform mutation in the TWIK-1 coding sequence, changing the 161 Thr codon into a codon for alanine. The product of the PCR was linearized by the enzyme BamHI and the cRNA were synthesized using a T7 RNA polymerase (Stratagene). Preparation of the *X. laevis* oocytes and cRNA injection were carried out in accordance with the literature (Guillemare, E. et al., 1992, *Biochemistry*, 31, 12463–12468.

Electrophysiological Measurements

In a 0.3-ml perfusion chamber, a single oocyte was impaled on two standard glass microelectrodes (0.5–2.0 MW) charged with 3 M KCl and maintained under voltage-clamp with a Dagan TEV200 amplifier. The bath solution contained 98 mM KCl, 1.8 mM CaCl$_2$, 2 mM MgCl$_2$ and 5 mM HEPES at pH 7.4 with KOH. Stimulation of the preparation, data acquisition and analyses were carried out with the pClamp program (Axon Instruments, USA).

For the patch-clamp experiments, the vitelline membrane was removed from the oocytes as described in the literature (Duprat, F. et al., 1995, *Biochem. Biophys. Res. Commun.*, 212, 657–663); the oocytes were then placed in a bath solution containing 140 mM KCl, 1.8 mM CaCl$_2$, 2 mM MgCl$_2$ and 5 mM HEPES at pH 7.4 with KOH. The pipettes were filled with a strong K$^+$ solution (40 mM KCl, 100 mM of potassium methane sulfonate, 1.8 mM CaCl$_2$, 2 mM MgCl$_2$ and 5 mM HEPES adjusted to pH 7.4 with KOH). 100 µM of GdCl$_3$ was added to the pipette solution to inhibit the action of the activated channels. The inside-out patches were perfused with a solution containing 140 mM KCl, 10 mM CaCl$_2$, 5 mM HEPES adjusted to pH 7.2 with KOH and 5 mM EGTA added daily. The single channel signals were filtered at 3.5 kHz and analyzed with the Biopatch program (Bio-Logic, Grenoble, France).

We claim:

1. An isolated and purified nucleic acid molecule encoding a mammalian protein which comprises 2 P domains and 4 transmembrane segments, and is competent to transport potassium across a membrane.

2. An isolated and purified nucleic acid molecule encoding a human protein which comprises 2 P domains and 4 transmembrane segments, and is competent to transport potassium across a membrane.

3. The nucleic acid molecule of claim 2 encoding a human protein which exhibits weak inward rectification.

4. The nucleic acid molecule of claim 3 which is expressed in brain and heart tissue and in addition, in at least one of the following tissues: placenta, liver, skeletal, muscle, kidney and pancreas.

5. The human nucleic acid sequence of claim 2 which comprises the sequence represented by SEQ ID No. 1.

6. A self replication vector comprising the nucleic acid molecule of claim 2.

7. A cell transformed with the self replicating vector of claim 6, which cell expresses a human protein which comprises 2 P domains and 4 transmembrane segments, and is competent to transport potassium across a membrane.

8. A micro-injected cell comprising the RNA transcript synthesized from the nucleic acid molecule of claim 2, which cell expresses a human protein which comprises 2 P domains and 4 transmembrane segments, and is competent to transport potassium across a membrane.

9. The transformed cell of claim 7, which cell is selected from the group consisting of prokaryotes and eukaryotes.

10. The transformed cell of claim 9 which is a bacterium.

11. The transformed cell of claim 10 which is a yeast, insect, plant or mammalian cell.

12. A method for the production of a human protein competent to transport potassium across a membrane which comprises 2 P domains and 4 transmembrane segments, comprising transferring the vector of claim 6 into a cellular host, culturing the cellular host under conditions allowing the production of said potassium channel, and purifying the human potassium channel.

13. The method of claim 12 wherein the cellular host is selected from the group consisting of prokaryotes and eukaryotes.

14. A pharmaceutical composition for the compensation of a deficiency in potassium channels at the level of one or more tissues, which comprises an isolated and purified nucleic acid molecule encoding a human protein comprising 2 P domains and 4 transmembrane segments which protein is competent to transport potassium across a membrane.

15. A pharmaceutical composition which comprises human cells transformed with the nucleic acid molecule of claim 2.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 1894 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 183..1190

(xi) SEQUENCE DESCRIPTION: SEQ ID NO:1:

```
GGGCAGGAAG ACGGCGCTGC CCGGAGGAGC GGGGCGGGCG GGCGCGCGGG GGAGCGGGCG         60

GCGGGCGGGA GCCAGGCCCG GGCGGGGGCG GGGGCGGCGG GGCCAGAAGA GGCGGCGGGC        120

CGCGCTCCGG CCGGTCTGCG GCGTTGGCCT TGGCTTTGGC TTTGGCGGCG GCGGTGGAGA        180

AG ATG CTG CAG TCC CTG GCC GGC AGC TCG TGC GTG CGC CTG GTG GAG          227
   Met Leu Gln Ser Leu Ala Gly Ser Ser Cys Val Arg Leu Val Glu
   1               5                  10                  15

CGG CAC CGC TCG GCC TGG TGC TTC GGC TTC CTG GTG CTG GGC TAC TTG         275
Arg His Arg Ser Ala Trp Cys Phe Gly Phe Leu Val Leu Gly Tyr Leu
                20                  25                  30

CTC TAC CTG GTC TTC GGC GCA GTG GTC TTC TCC TCG GTG GAG CTG CCC         323
Leu Tyr Leu Val Phe Gly Ala Val Val Phe Ser Ser Val Glu Leu Pro
            35                  40                  45

TAT GAG GAC CTG CTG CGC CAG GAG CTG CGC AAG CTG AAG CGA CGC TTC         371
Tyr Glu Asp Leu Leu Arg Gln Glu Leu Arg Lys Leu Lys Arg Arg Phe
        50                  55                  60

TTG GAG GAG CAC GAG TGC CTG TCT GAG CAG CAG CTG GAG CAG TTC CTG         419
Leu Glu Glu His Glu Cys Leu Ser Glu Gln Gln Leu Glu Gln Phe Leu
    65                  70                  75

GGC CGG GTG CTG GAG GCC AGC AAC TAC GGC GTG TCG GTG CTC AGC AAC         467
Gly Arg Val Leu Glu Ala Ser Asn Tyr Gly Val Ser Val Leu Ser Asn
80                  85                  90                  95

GCC TCG GGC AAC TGG AAC TGG GAC TTC ACC TCC GCG CTC TTC TTC GCC         515
Ala Ser Gly Asn Trp Asn Trp Asp Phe Thr Ser Ala Leu Phe Phe Ala
                100                 105                 110

AGC ACC GTG CTC TCC ACC ACA GGT TAT GGC CAC ACC GTG CCC TTG TCA         563
Ser Thr Val Leu Ser Thr Thr Gly Tyr Gly His Thr Val Pro Leu Ser
            115                 120                 125

GAT GGA GGT AAG GCC TTC TGC ATC ATC TAC TCC GTC ATT GGC ATT CCC         611
Asp Gly Gly Lys Ala Phe Cys Ile Ile Tyr Ser Val Ile Gly Ile Pro
        130                 135                 140

TTC ACC CTC CTG TTC CTG ACG GCT GTG GTC CAG CGC ATC ACC GTG CAC         659
Phe Thr Leu Leu Phe Leu Thr Ala Val Val Gln Arg Ile Thr Val His
    145                 150                 155

GTC ACC CGC AGG CCG GTC CTC TAC TTC CAC ATC CGC TGG GGC TTC TCC         707
Val Thr Arg Arg Pro Val Leu Tyr Phe His Ile Arg Trp Gly Phe Ser
160                 165                 170                 175

AAG CAG GTG GTG GCC ATC GTC CAT GCC GTG CTC CTT GGG TTT GTC ACT         755
Lys Gln Val Val Ala Ile Val His Ala Val Leu Leu Gly Phe Val Thr
                180                 185                 190

GTG TCC TGC TTC TTC TTC ATC CCG GCC GCT GTC TTC TCA GTC CTG GAG         803
Val Ser Cys Phe Phe Phe Ile Pro Ala Ala Val Phe Ser Val Leu Glu
            195                 200                 205

GAT GAC TGG AAC TTC CTG GAA TCC TTT TAT TTT TGT TTT ATT TCC CTG         851
Asp Asp Trp Asn Phe Leu Glu Ser Phe Tyr Phe Cys Phe Ile Ser Leu
        210                 215                 220

AGC ACC ATT GGC CTG GGG GAT TAT GTG CCT GGG GAA GGC TAC AAT CAA         899
Ser Thr Ile Gly Leu Gly Asp Tyr Val Pro Gly Glu Gly Tyr Asn Gln
```

```
           225                 230                 235
AAA TTC AGA GAG CTC TAT AAG ATT GGG ATC ACG TGT TAC CTG CTA CTT         947
Lys Phe Arg Glu Leu Tyr Lys Ile Gly Ile Thr Cys Tyr Leu Leu Leu
240                 245                 250                 255

GGC CTT ATT GCC ATG TTG GTA GTT CTG GAA ACC TTC TGT GAA CTC CAT         995
Gly Leu Ile Ala Met Leu Val Val Leu Glu Thr Phe Cys Glu Leu His
                260                 265                 270

GAG CTG AAA AAA TTC AGA AAA ATG TTC TAT GTG AAG AAG GAC AAG GAC        1043
Glu Leu Lys Lys Phe Arg Lys Met Phe Tyr Val Lys Lys Asp Lys Asp
            275                 280                 285

GAG GAT CAG GTG CAC ATC ATA GAG CAT GAC CAA CTG TCC TTC TCC TCG        1091
Glu Asp Gln Val His Ile Ile Glu His Asp Gln Leu Ser Phe Ser Ser
        290                 295                 300

ATC ACA GAC CAG GCA GCT GGC ATG AAA GAG GAC CAG AAG CAA AAT GAG        1139
Ile Thr Asp Gln Ala Ala Gly Met Lys Glu Asp Gln Lys Gln Asn Glu
    305                 310                 315

CCT TTT GTG GCC ACC CAG TCA TCT GCC TGC GTG GAT GGC CCT GCA AAC        1187
Pro Phe Val Ala Thr Gln Ser Ser Ala Cys Val Asp Gly Pro Ala Asn
320                 325                 330                 335

CAT TGAGCGTAGG ATTTGTTGCA TTATGCTAGA GCACCAGGGT CAGGGTGCAA             1240
His

GGAAGAGGCT TAAGTATGTT CATTTTTATC AGAATGCAAA AGCGAAAATT ATGTCACTTT      1300

AAGAAATAGC TACTGTTTGC AATGTCTTAT TAAAAAACAA CAAAAAAAGA CACATGGAAC      1360

AAAGAAGCTG TGACCCCAGC AGGATGTCTA ATATGTGAGG AAATGAGATG TCCACCTAAA      1420

ATTCATATGT GACAAAATTA TCTCGACCTT ACATAGGAGG AGAATACTTG AAGCAGTATG      1480

CTGCTGTGGT TAGAAGCAGA TTTTATACTT TTAACTGGAA ACTTTGGGGT TTGCATTTAG      1540

ATCATTTAGC TGATGGCTAA ATAGCAAAAT TTATATTTAG AAGCAAAAAA AAAAAGCATA      1600

GAGATGTGTT TTATAAATAG GTTTATGTGT ACTGGTTTGC ATGTACCCAC CCAAAATGAT      1660

TATTTTTGGA GAATCTAAGT CAAACTCACT ATTTATAATG CATAGGTAAC CATTAACTAT      1720

GTACATATAA AGTATAAATA TGTTTATATT CTGTACATAT GGTTTAGGTC ACCAGATCCT      1780

AGTGTAGTTC TGAAACTAAG ACTATAGATA TTTTGTTTCT TTTGATTTCT CTTTATACTA      1840

AAGAATCCAG AGTTGCTACA ATAAAATAAG GGGAATAATA AAAAAAAAAA AAAA            1894

(2) INFORMATION FOR SEQ ID NO:2:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Gln Ser Leu Ala Gly Ser Ser Cys Val Arg Leu Val Glu Arg
1               5                   10                  15

His Arg Ser Ala Trp Cys Phe Gly Phe Leu Val Leu Gly Tyr Leu Leu
            20                  25                  30

Tyr Leu Val Phe Gly Ala Val Val Phe Ser Ser Val Glu Leu Pro Tyr
        35                  40                  45

Glu Asp Leu Leu Arg Gln Glu Leu Arg Lys Leu Lys Arg Arg Phe Leu
    50                  55                  60

Glu Glu His Glu Cys Leu Ser Glu Gln Gln Leu Glu Gln Phe Leu Gly
65                  70                  75                  80

Arg Val Leu Glu Ala Ser Asn Tyr Gly Val Ser Val Leu Ser Asn Ala
                85                  90                  95
```

```
Ser Gly Asn Trp Asn Trp Asp Phe Thr Ser Ala Leu Phe Phe Ala Ser
            100                 105                 110

Thr Val Leu Ser Thr Thr Gly Tyr Gly His Thr Val Pro Leu Ser Asp
        115                 120                 125

Gly Gly Lys Ala Phe Cys Ile Ile Tyr Ser Val Ile Gly Ile Pro Phe
        130                 135             140

Thr Leu Leu Phe Leu Thr Ala Val Val Gln Arg Ile Thr Val His Val
145                 150                 155                 160

Thr Arg Arg Pro Val Leu Tyr Phe His Ile Arg Trp Gly Phe Ser Lys
                165                 170                 175

Gln Val Val Ala Ile Val His Ala Val Leu Leu Gly Phe Val Thr Val
                180                 185                 190

Ser Cys Phe Phe Phe Ile Pro Ala Ala Val Phe Ser Val Leu Glu Asp
        195                 200                 205

Asp Trp Asn Phe Leu Glu Ser Phe Tyr Phe Cys Phe Ile Ser Leu Ser
        210                 215                 220

Thr Ile Gly Leu Gly Asp Tyr Val Pro Gly Glu Gly Tyr Asn Gln Lys
225                 230                 235                 240

Phe Arg Glu Leu Tyr Lys Ile Gly Ile Thr Cys Tyr Leu Leu Leu Gly
                245                 250                 255

Leu Ile Ala Met Leu Val Val Leu Glu Thr Phe Cys Glu Leu His Glu
                260                 265                 270

Leu Lys Lys Phe Arg Lys Met Phe Tyr Val Lys Asp Lys Asp Glu
                275                 280                 285

Asp Gln Val His Ile Ile Glu His Asp Gln Leu Ser Phe Ser Ser Ile
        290                 295                 300

Thr Asp Gln Ala Ala Gly Met Lys Glu Asp Gln Lys Gln Asn Glu Pro
305                 310                 315                 320

Phe Val Ala Thr Gln Ser Ser Ala Cys Val Asp Gly Pro Ala Asn His
                325                 330                 335

(2) INFORMATION FOR SEQ ID NO:3:

(i) SEQUENCE CHARACTERISTICS:
        (A) LENGTH: 347 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Tyr Thr Asp Glu Gly Glu Tyr Ser Gly Asp Thr Asp His Gly Gly
1               5                   10                  15

Ser Thr Met Gln Lys Met Ser Pro Asn Thr Arg Gln Asn Phe Arg Gln
                20                  25                  30

Asn Val Asn Val Val Cys Leu Ser Ala Ala Ile Thr Leu Leu Val
            35                  40                  45

Phe Asn Leu Ile Gly Ala Gly Ile Phe Tyr Leu Ala Glu Thr Gln Asn
        50                  55                  60

Ser Ser Glu Ser Leu Asn Glu Asn Ser Glu Val Ser Lys Cys Leu His
65                  70                  75                  80

Asn Leu Pro Ile Gly Gly Lys Ile Thr Ala Glu Met Lys Ser Lys Leu
                85                  90                  95

Gly Lys Cys Leu Thr Lys Ser Ser Arg Ile Asp Gly Phe Gly Lys Ala
                100                 105                 110
```

```
Ile Phe Phe Ser Trp Thr Leu Tyr Ser Thr Val Gly Tyr Gly Ser Leu
            115                 120                 125

Tyr Pro His Ser Thr Leu Gly Arg Tyr Leu Thr Ile Phe Tyr Ser Leu
130                     135                 140

Leu Met Ile Pro Val Phe Ile Ala Phe Lys Phe Glu Phe Gly Thr Phe
145                 150                 155                 160

Leu Ala His Phe Leu Val Val Ser Asn Arg Thr Arg Leu Ala Val
                165                 170                 175

Lys Lys Ala Tyr Tyr Lys Leu Ser Gln Asn Pro Glu Asn Ala Glu Thr
            180                 185                 190

Pro Ser Asn Ser Leu Gln His Asp Tyr Leu Ile Phe Leu Ser Ser Leu
            195                 200                 205

Leu Leu Cys Ser Ile Ser Leu Leu Ser Ser Ala Leu Phe Ser Ser
        210                 215                 220

Ile Glu Asn Ile Ser Tyr Leu Ser Ser Val Tyr Phe Gly Ile Ile Thr
225                 230                 235                 240

Met Phe Leu Ile Gly Ile Gly Asp Ile Val Pro Thr Asn Leu Val Trp
                245                 250                 255

Phe Ser Gly Tyr Cys Met Leu Phe Leu Ile Ser Asp Val Leu Ser Asn
                260                 265                 270

Gln Ile Phe Tyr Phe Cys Gln Ala Arg Val Arg Tyr Phe Phe His Ile
            275                 280                 285

Leu Ala Arg Lys Ile Leu Leu Leu Arg Glu Glu Asp Asp Gly Phe Gln
290                 295                 300

Leu Glu Thr Thr Val Ser Leu Gln His Ile Pro Ile Ile Asn Ser Gln
305                 310                 315                 320

Cys Met Pro Ser Leu Val Leu Asp Cys Glu Lys Glu Glu Leu Asp Asn
                325                 330                 335

Asp Glu Lys Leu Ile Ser Ser Leu Thr Ser Thr
            340                 345

(2) INFORMATION FOR SEQ ID NO:4:

(i) SEQUENCE CHARACTERISTICS:
        (A) LENGTH: 383 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Met Thr Val Ser Met Glu Glu Asn Ser Lys Ile Gln Met Leu Ser Ala
1               5                   10                  15

Thr Ser Lys Asp Lys Val Ala Thr Asp Arg Ser Leu Leu Asn Lys
            20                  25                  30

Tyr His Leu Gly Pro Leu Ala Leu His Thr Gly Leu Val Leu Ser Cys
            35                  40                  45

Val Thr Tyr Ala Leu Gly Gly Ala Tyr Leu Phe Leu Ser Ile Glu His
        50                  55                  60

Pro Glu Glu Leu Lys Arg Arg Glu Lys Ala Ile Arg Glu Phe Gln Asp
65                  70                  75                  80

Leu Lys Gln Gln Phe Met Gly Asn Ile Thr Ser Gly Ile Glu Asn Ser
                85                  90                  95

Glu Gln Ser Ile Glu Ile Tyr Thr Lys Lys Leu Ile Leu Met Leu Glu
            100                 105                 110

Asp Ala His Asn Ala His Ala Phe Glu Tyr Phe Phe Leu Asn His Glu
```

```
                115                 120                 125
Ile Pro Lys Asp Met Trp Thr Phe Ser Ser Ala Leu Val Phe Thr Thr
    130                 135                 140

Thr Thr Val Ile Pro Val Gly Tyr Gly Tyr Ile Phe Pro Val Ser Ala
145                 150                 155                 160

Tyr Gly Arg Met Cys Leu Ile Ala Tyr Ala Leu Leu Gly Ile Pro Leu
                165                 170                 175

Thr Leu Val Thr Met Ala Asp Thr Gly Lys Phe Ala Ala Gln Leu Val
            180                 185                 190

Thr Arg Trp Phe Gly Asp Asn Asn Met Ala Ile Pro Ala Ala Ile Phe
        195                 200                 205

Val Cys Leu Leu Phe Ala Tyr Pro Leu Val Val Gly Phe Ile Leu Cys
    210                 215                 220

Ser Thr Ser Asn Ile Thr Tyr Leu Asp Ser Val Tyr Phe Ser Leu Thr
225                 230                 235                 240

Ser Ile Phe Thr Ile Gly Phe Gly Asp Leu Thr Pro Asp Met Asn Val
                245                 250                 255

Ile His Met Val Leu Phe Leu Ala Val Gly Val Ile Leu Val Thr Ile
            260                 265                 270

Thr Leu Asp Ile Val Ala Ala Glu Met Ile Asp Arg Val His Tyr Met
        275                 280                 285

Gly Arg His Val Gly Lys Ala Lys Glu Leu Ala Gly Lys Met Phe Gln
    290                 295                 300

Leu Ala Gln Ser Leu Asn Met Lys Gln Gly Leu Val Ser Gly Val Gly
305                 310                 315                 320

Gln Leu His Ala Leu Ala Arg Phe Gly Met Leu Val Gly Arg Glu Glu
                325                 330                 335

Val Asp Lys Thr Gln Glu Asp Gly Ile Ile Ala Phe Ser Pro Asp Val
            340                 345                 350

Met Asp Gly Leu Glu Phe Met Asp Thr Leu Ser Ile Tyr Ser Arg Arg
        355                 360                 365

Ser Arg Arg Ser Ala Glu Asn Ser Ala Arg Asn Leu Phe Leu Ser
    370                 375                 380
```

(2) INFORMATION FOR SEQ ID NO:5:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Phe Thr Ser Ala Leu Phe Phe Ala Ser Thr Val Leu Ser Thr Thr Gly
1               5                   10                  15

Tyr Gly His Thr Val Pro Leu Ser Asp Gly Gly
                20                  25
```

(2) INFORMATION FOR SEQ ID NO:6:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Phe Leu Glu Ser Phe Tyr Phe Cys Phe Ile Ser Leu Ser Thr Ile Gly
1               5                   10                  15

Leu Gly Asp Tyr Val Pro Gly Glu Gly Tyr Asn
            20                  25

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Tyr Phe Asn Cys Ile Tyr Phe Cys Phe Leu Cys Leu Leu Thr Ile Gly
1               5                   10                  15

Tyr Gly Asp Tyr Ala Pro Arg Thr Gly Ala Gly
            20                  25

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Tyr Gly Asn Ala Leu Tyr Phe Cys Thr Val Ser Leu Leu Thr Val Gly
1               5                   10                  15

Leu Gly Asp Ile Leu Pro Lys Ser Val Gly Ala
            20                  25

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Tyr Trp Thr Cys Val Tyr Phe Leu Ile Val Thr Met Ser Thr Val Gly
1               5                   10                  15

Tyr Gly Asp Val Tyr Cys Glu Thr Val Leu Gly
            20                  25

(2) INFORMATION FOR SEQ ID NO:10:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Ile Pro Asp Ala Phe Trp Trp Ala Val Val Thr Met Thr Thr Val Gly
1               5                   10                  15

Tyr Gly Asp Met Thr Pro Val Gly Phe Trp Gly
            20                  25

(2) INFORMATION FOR SEQ ID NO:11:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Ile Pro Glu Ala Phe Trp Trp Ala Gly Ile Thr Met Thr Thr Val Gly
1               5                   10                  15
Tyr Gly Asp Ile Cys Pro Thr Thr Ala Leu Gly
            20                  25

(2) INFORMATION FOR SEQ ID NO:12:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Ile Pro Ala Ala Phe Trp Tyr Thr Ile Val Thr Met Thr Thr Leu Gly
1               5                   10                  15
Tyr Gly Asp Met Val Pro Glu Thr Ile Ala Gly
            20                  25

(2) INFORMATION FOR SEQ ID NO:13:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Ile Pro Leu Gly Leu Trp Trp Ala Leu Val Thr Met Thr Thr Val Gly
1               5                   10                  15
Tyr Gly Asp Met Ala Pro Lys Thr Tyr Ile Gly
            20                  25

(2) INFORMATION FOR SEQ ID NO:14:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Tyr Val Thr Ala Leu Tyr Trp Ser Ile Thr Thr Leu Thr Thr Thr Gly
1               5                   10                  15
Tyr Gly Asp Phe His Ala Glu Asn Pro Arg Glu
            20                  25

(2) INFORMATION FOR SEQ ID NO:15:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Tyr Val Thr Ser Met Tyr Trp Ser Ile Thr Thr Leu Thr Thr Val Gly
1               5                  10                  15
Tyr Gly Asp Leu His Pro Val Asn Thr Lys Glu
            20                  25
```

(2) INFORMATION FOR SEQ ID NO:16:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Tyr Val Thr Ala Leu Tyr Phe Thr Met Thr Cys Met Thr Ser Val Gly
1               5                  10                  15
Phe Gly Asn Val Ala Ala Glu Thr Asp Asn Glu
            20                  25
```

(2) INFORMATION FOR SEQ ID NO:17:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Met Thr Ser Ala Phe Leu Phe Ser Leu Glu Thr Gln Val Thr Ile Gly
1               5                  10                  15
Tyr Gly Phe Arg Phe Val Thr Glu Gln Cys Ala
            20                  25
```

(2) INFORMATION FOR SEQ ID NO:18:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Phe Thr Ala Ala Phe Leu Phe Ser Ile Glu Thr Gln Thr Thr Ile Gly
1               5                  10                  15
Tyr Gly Phe Arg Cys Val Thr Asp Glu Cys Pro
            20                  25
```

(2) INFORMATION FOR SEQ ID NO:19:

(i) SEQUENCE CHARACTERISTICS:

```
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Phe Pro Ser Ala Phe Leu Phe Phe Ile Glu Thr Glu Ala Thr Ile Gly
1               5                   10                  15

Tyr Gly Tyr Arg Tyr Ile Thr Asp Lys Cys Pro
            20                  25
```